United States Patent [19]

Cavalier et al.

[11] Patent Number: 4,562,205

[45] Date of Patent: Dec. 31, 1985

[54] DERIVATIVES OF 2-AMINOACETIC ACID

[75] Inventors: Robert G. Cavalier, Rixensart; Alexis A. Cordi, Gistoux; Claude L. Gillet, Blanmont; Philippe M. Janssens de Varebeke, Bossut-Gottechain; Paul J. Niebes, Grez-Doiceau; Joseph L. Roba, Dion-Valmont; William R. Van Dorsser, Court-St-Etienne; Georges E. Lambelin; Michel R. Franz, both of Brussels, all of Belgium

[73] Assignee: Continental Pharma Inc., Brussels, Belgium

[21] Appl. No.: 624,110

[22] Filed: Jun. 25, 1984

[30] Foreign Application Priority Data

Jun. 30, 1983 [LU] Luxembourg ..................... 84891

[51] Int. Cl.$^4$ .......................................... A61K 31/195
[52] U.S. Cl. .................................... 514/546; 562/575
[58] Field of Search .................. 562/575; 424/319; 514/546

[56] References Cited

U.S. PATENT DOCUMENTS 4,372,974 2/1983 Fish et al. .......................... 424/319
4,397,866 8/1983 Wurtman .......................... 424/319

FOREIGN PATENT DOCUMENTS 2145402 4/1973 France .
2320089 6/1977 France .
2422400 2/1979 France .

OTHER PUBLICATIONS

Patent Abstracts of Japan, Unexamined Applications, Section C, vol. 6, No. 169, Sep. 2, 1982, p. 80 C 122, Kokai No. 57-85 321 (Kiyonto Yakuhin Kogyo K.K.).
Katz et al., "Formation of Propionyl-, Butyryl-, and Other Acylglycines by Enzymes of Clostridium Kluyveri", Journal Biol. Chem., vol. 200, pp. 431–441, 1953.
Suemitsu et al., "The Structures of Two New Glycine Conjugated Compounds from Cattle Urine", Agr. Biol. Chem., vol. 38(4), pp. 885–886, 1974.
Ramsdell et al., "Gas Chromatographic Retention Indices of Twenty Metabolically Important Acylglycines as Trimethylsilyl Derivatives", Journal of Chromatography, vol. 181, pp. 90–94, 1980.
Tjoa et al., "Acylglycines, the Gas Chromatograph-/Mass Spectrometric Identification and Interpretation of Their Spectra", Clinica Chimica Acta, vol. 95, pp. 35–45, 1979.
Roberts, "y-Aminobutyric Acid and Nervous System Function–A Perspective", Biochemical Pharmacology, vol. 23, pp. 2637–2649, 1974.
Turner, "The Organization of Screening" from Screening Methods in Pharmacology, Academic Press 1965, pp. 22–34.
Litchfield, Fr. et al., "A Simplified Method of Evaluating Dose–Effect Experiments", J. Pharmacology Exr. Theap., vol. 96, pp. 99–113, 1949.

*Primary Examiner*—Michael L. Shippen
*Attorney, Agent, or Firm*—Cushman, Darby & Cushman

[57] ABSTRACT

2-Pentanoylaminoacetic acid and pharmaceutically suitable salts thereof are claimed for use as pharmaceuticals.

The compounds are useful in producing an effect on the central nervous system, especially in the treatment of various forms of epilepsy, of disninesiae, of parkinsonism, of memory troubles, of psychic troubles and of cerebral anoxia.

8 Claims, No Drawings

DERIVATIVES OF 2-AMINOACETIC ACID

This invention relates to 2-pentanoylaminoacetic acid (I) and to pharmaceutical acceptable metal salts and addition salts with bases derived thereof, for use as pharmaceuticals.

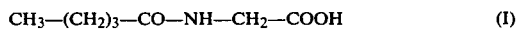

$$CH_3-(CH_2)_3-CO-NH-CH_2-COOH \qquad (I)$$

The metal salts may be, for example, a sodium, a potassium, a lithium, a calcium, a magnesium, an aluminium or an iron salt. The addition salts may be formed by reaction with an inorganic base such as ammonia, or with an organic base which may be an aliphatic, a cycloaliphatic or an heterocyclic base, such as, for example, ethylamine, diethylamine, triethylamine, isopropylamine, ethanolamine, diethanolamine, triethanolamine. Said organic base may also be an amino-acid natural or not, such as, for example, lysine, ornithine or arginine.

A preferred salt of 2-pentanoylaminoacetic acid is the sodium salt.

1. BACKGROUND OF THE INVENTION

The compound of the present invention, 2-pentanoylaminoacetic acid, is known for several years.

The publication of J. Katz et al., [C.A., 47, 3927i (1953); J. Biol. Chem., 200, 431–441 (1953)] describes the preparation of compound I.

In the form of its methyl ester, compound (I) has been isolated from cattle urine, and its structure has been confirmed by synthesis [S. Rikisaku et al., C.A. 81, 102,235v (1974); Agr. Biol. Chem., 38, 885–6 (1974)]. Other publications describe the synthesis of several acylglycines amongst which compound I, and the analysis of a mixture of these acylglycine derivatives by gaschromatography-mass spectroscopy techniques, e.g. H. S. Ramsdell et al., J. Chromatogr., 181, 90–94 (1980); S. S. Tjoa et al., Clin. Chim. Acta, 95, 35–45 (1979).

However no biological activity of 2-pentanoylaminoacetic acid has been disclosed so far.

II. DESCRIPTION OF THE INVENTION

It has surprisingly been found by the inventors that compound I and pharmaceutical acceptable salts thereof exhibit a potent anti-convulsant activity against convulsions induced by bicuculline in mice.

This observation indicates that 2-pentanoylaminoacetic acid produces an effect on the central nervous system and in particular on the GABA-system, because as a matter of fact, bicuculline is known to be a specific antagonist of GABA (4-aminobutyric acid) [E. Roberts, Biochem. Pharmacol., 23, 2637–2649 (1974)].

It is clear that has also been found pharmaceutical compositions comprising compound I or a pharmaceutically acceptable salt thereof present great interest for producing an effect on the central nervous system, in particular in the treatment of various forms of epilepsy, in the treatment of dyskinesiae such as, for example, parkinsonism, in the treatment of memory troubles, of psychic troubles such as, for example, depression, and in the treatment of cerebral anoxia.

The activity of 2-pentanoylaminoacetic acid and pharmaceutically acceptable salts thereof has been evidenced by the pharmacological tests described hereinafter.

II.1. Anti-convulsant activity

The compounds tested, 2-pentanoylaminoacetic acid (compound I), sodium 2-pentanoylaminoacetate (compound II) or sodium valproate (a generally accepted reference substance), have been administered orally to 20 mice (CD1-Charles River) at a dose of 10 mg/kg as a suspension in a 1% tragacanth gum mucilage. Administration has been done by means of an intragastric tube.

Three hours later, bicuculline has been administered at a dose of 0,7 mg/kg by intravenous injection in the lateral vein of the tail.

The number of animals which exhibit tonic extension has been noted and the results of the test are represented in the form of "percentage of protection", i.e. the percentage of the animals which have been protected against tonic extension.

The results obtained are given hereinafter and they clearly indicate that a potent anticonvulsant activity is effected by the drugs tested.

| Compound. | % of protection. |
| --- | --- |
| 2-pentanoylaminoacetic acid (I) | 55 |
| sodium 2-pentanoylaminoacetate (II) | 55 |
| sodium valproate | 40 |

The anti-convulsant activity of the compounds has been further evaluated, using the technique described hereinabove, by examining the effect at different doses. From the experimental data, the $ED_{50}$ value has been calculated, i.e. the effective dose (mg/kg) providing protection against tonic extension of 50% of the animals. The results obtained are the following:

| Compound | $ED_{50}$ (mg/kg) |
| --- | --- |
| 2-pentanoylaminoacetic acid (I) | 10.7 |
| sodium 2-pentancylaminoacetate (II) | 9.2 |
| sodium valproate | 29.0 |

These data indicate that 2-pentanoylaminoacetic acid and its sodium salt are more potent than sodium in this test.

II.2. Toxicity

In further pharmacological tests the acute toxicity and the effect on behaviour have been examined. The effect on behaviour has been studied using a method derived from the one of S. Irvin [Gordon Res. Conf. on Medicinal Chemistry, p. 1933 (1959) as cited by R. A. Turner (Screening Methods in Pharmacology, Acad. Press, 1965, Chapter III, pages 22–34)].

The drug to be tested has been administered orally as a 1% tragacanth gum mucilage, by means of an intragastric tube to groups of 3 or 5 mice, fasted for 18 hours. The compounds have been tested at a dose decreasing in a logarithmic way, starting from 3000 mg/kg, i.e. 3000, 1000, 300, 100, 30 and 10 mg/kg. No further testing has been made when a dose has been reached at which no abnormal behaviour or toxicity has been observed. Behaviour has been studied 2, 4, 6 and 24 hours after treatment and the observation has been extended if symptoms persisted at that moment. The deaths were registered for 14 days following the treatment. These observations allowed to determine the MTD value, i.e. the maximal tolerated dose, which is the maximal dose (mg/kg) which does not induce side effects or toxicity. The data so obtained are the following:

| Compound | MTD mg/kg |
| --- | --- |
| 2-pentanoylaminoacetic acid (I) | ≧3000 |
| sodium 2-pentanoylaminoacetate (II) | ≧3000 |
| sodium valproate | 30 |

The LD$_{50}$ value, i.e. the dose expressed in mg/kg which is lethal for 50% of the animals, has been calculated according to the Litchfield and Wilcoxon method [J. Pharmacol. Exp. Ther., 96, 99 (1949)].
The results obtained are shown hereinafter:

| Compound | LD$_{50}$ mg/kg |
| --- | --- |
| 2-pentanoylaminoacetic acid (I) | >3000 |
| sodium 2-pentanoylaminoacetate (II) | >3000 |
| sodium valproate | 2250 |

It clearly results from these data that the toxicity and the effect on behaviour of 2-pentanoylaminoacetic acid and its sodium salt are very weak and it has to be noticed that at a dose of 3000 mg/kg per os no deaths have been observed for none of both compounds.

Hence 2-pentanoylaminoacetic acid and its sodium salt are better than sodium valproate; their superiority is evidenced quantitatively by means of the therapeutical indexes TI-A and TI-B which corresponds, respectively, to the ratio of the LD$_{50}$/ED$_{50}$ values and to the ratio of the MTD/ED$_{50}$ values. The values of these therapeutical indexes are the following:

| Compound | TI-A (LD$_{50}$/ED$_{50}$) | TI-B (MTD/ED$_{50}$) |
| --- | --- | --- |
| 2-pentanoylamino-acetic acid (I) | >280 | >280 |
| sodium 2-pentanoylamino-acetate (II) | >326 | >326 |
| sodium valproate | 78 | 1 |

The pharmacological data mentioned hereinbefore are evidencing the presence of potent anti-convulsant activity combined with weak toxicity and, hence, are emphasizing the pharmaceutical interest of 2-pentanoylaminoacetic acid and its suitable salts.

Compound I, 2-pentanoylaminoacetic acid, can be prepared by various art-known methods, one of which is indicated in scheme 1, hereinafter, given as a non limiting example.

Scheme 1.

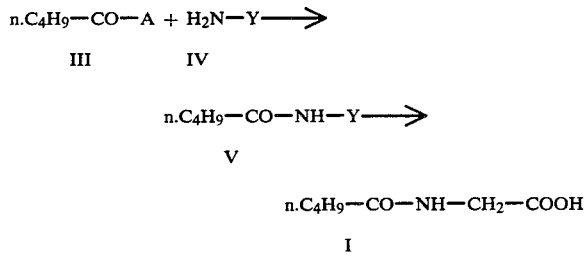

In formula III, A is such that the radical —CO—A represents, for example, a carboxylic group, an alkoxycarbonyl group, an acide halide group, an anhydride group, a carbamoyl group or a N-carbonylimidazole group.

In formula IV and V, Y represents: either the CH$_2$—COOH group, either a precursor of said CH$_2$—COOH group, such as:
the —CH$_2$—Z group wherein Z represents, for example, an alkoxycarbonyl group or a formyl group optionally used in a protected form such as, e.g. a dithioacetal group, which may be cyclic or not.
the

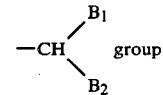

wherein B$_1$ and B$_2$, which can be identical or not, represent, for example, an alkoxycarbonyl group on a carboxylic group.

According to the nature of the functional groups and to the reaction conditions, the acylation of amine IV by reagent III can directly yield compound I or a salt thereof, or yield intermediate V, which optionally can be isolated or not, before it is converted into compound I or a salt thereof.

According to the nature of the —CO—A group, the acylation is usually carried out by reacting compound III with at least two equivalents of amine IV, or with one equivalent of amine IV and at least one equivalent of an organic or inorganic base, such as, for example, a tertiary amine, pyridine, an hydroxyde or a carbonate of an alkali or earthalkali metal. Usually, the reaction is carried out in an inert solvent or an excess of the organic base is used as solvent. If the —CO—A group, in reagent III, represents a carboxylic group, then the acylation of compound IV is classically made in the presence of a dehydrating agent such as, for example, phosphorus pentoxyde, or of a coupling agent such as, for example, dicyclohexylcarbodiimide or 1,1'-carbonylidiimidazole. If Y, in the intermediate V, represents a precursor of the —CH$_2$—COOH group, it is converted into said carboxymethyl group by well-known methods, chosen according to the nature of the group Y, such as, for example:

by hydrolysis, carried out in an aqueous or alcoholic-aqueous medium in the presence of an acidic or basic catalyst, by oxydation, optionally combined with hydrolysis or proceeded by deprotection of the functional group, by decarboxylation in acidic medium at elevated temperature, optionally proceeded by hydrolysis.

It is clear that all reagents and reaction conditions used to achieve the acylation of compound IV and the conversion of compound V into compound I have to be chosen in such a way as to avoid undesired secondary reactions or degradation of the molecule. In case 2-pentanoylaminoacetic acid is obtained as the free carboxylic acid it can easily be converted by art-known methods into its suitable metal salts, for example, by treatment in aqueous medium with the corresponding metal hydroxydes, carbonates or bicarbonates, or into its suitable addition salts by reaction in an inert solvent with the corresponding organic base. If, on the contrary, 2-pentanoylaminoacetic acid is obtained in the form of a metal or an addition salt, it can be transformed into the free carboxylic form by treatment with a suitable acid. Conversion of one salt into another salt can also be made by art-known methods.

The preparation of 2-pentanoylaminoacetic acid and the sodium salt thereof is illustrated hereinafter by a non limiting example.

EXAMPLE 1

Synthesis of 2-pentanoylaminoacetic acid (compound I)

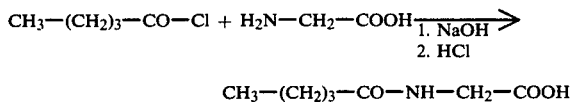

At 0° C., 10 g (0,133 mole) of glycine are dissolved in 33,3 ml 4N (0,133 mole) sodium hydroxyde. Then with vigourous stirring, 16 g (0,133 mole) pentanoylchloride and 33,3 ml 4N sodium hydroxyde (0,133 mole) are simultaneously added to the mixture. It is stirred until the characteristic smell of the acid chloride has disappeared, then acidified at 0° C. with concentrated hydrochloric acid and extracted with ethyl acetate. The organic solution is dried and the solvent is removed at diminished pressure. The residue is recrystallized from toluene, which yields 2-pentanoylaminoacetic acid.

Melting point: 82° C.

| Elemental analysis | C | H | N |
|---|---|---|---|
| % calculated | 52,82 | 8,23 | 8,50 |
| % found | 52,46 | 8,27 | 8,83 |

EXAMPLE 2

Synthesis of sodium 2-pentanoylaminoacetate (compound II)

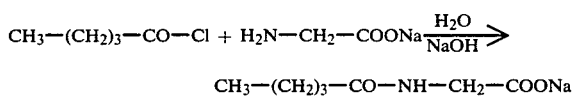

At 0° C., 10 g (0,133 mole) of glycine are dissolved in 33,3 ml 4N (0,133 mole) sodium hydroxyde. Then, with vigourous stirring, 16 g (0,133 mole) pentanoyl chloride and 33,3 mole 4N (0,133 mole) sodium hydroxyde are simultaneously added. The mixture is stirred until the characteristic smell of the acid chloride has disappeared, then all water is distilled off and the residue is extracted by boiling isopropanol. The first crop of the crystallization yields sodium pentanoate. The next crops, obtained by cooling of the isopropanol solution, yield crude sodium 2-pentanoylaminoacetate, which is purified by crystallization from ethanol.

Melting point: 190° C.

| Elemental analysis | C | H | N |
|---|---|---|---|
| % calculated | 46,40 | 6,67 | 7,73 |
| % found | 46,00 | 6,66 | 7,69 |

In view of the pharmaceutical use of 2-pentanoylaminoacetic acetic acid various pharmaceutical compositions may be formulated in order to be administered orally, rectally or parenterally, containing at least an effective amount of said compound or a salt thereof, usually in the presence of at least one pharmaceutical excipient. Thus, for example, the compositions to be administered orally can be liquids or solids and exist as tablets, sugar-coated pills, coated tablets, capsules, granules, powders, syrups or suspensions. The dry oral formulations comprise additives and excipients commonly used in galenic pharmacy, inert diluents, disintegration agents, binders and lubricants, such as lactose, starch, talc, gelatin, stearic acid, cellulose and derivatives thereof, silicilic acid, magnesium stearate, polyvinylpyrrolidone, calcium phosphate, calcium carbonate and the like.

Such preparations can be made in order to prolong disintegration and consequently the active duration of the active element.

The aqueous suspensions, the emulsions and the oily solutions are prepared in the presence of sweetening agents, such as dextrose or glycerol, flavouring agents, such as vanillin for example, and can also contain thickening agents, wetting agents and preservation agents.

The oily emulsions and solutions are prepared in an oil of vegetal or animal origin and can contain emulsifiers, flavouring, dispersing, sweetening and antioxidant agents. For parenteral administration, sterile water, an aqueous polyvinylpyrrolidone solution, peanut oil ethyl oleate and the like are used as a vehicle. These aqueous or oily injectable solutions can contain thickening, wetting, dispersing and gelling agents.

The compositions to be administered rectally may be solids or liquids and may be presented in the form of suppositories, of gels, of solutions, of emulsions or of suspensions.

The suppositories may be prepared using fats such as cacao butter or semi-synthetic substances derived from triglycerids, or using hydrosoluble products such as mixtures or polyethyleneglycols.

The daily dose for administration of compound I or a salt thereof will be 100 mg to 5 g. In order to facilitate their use and their administration, the aforementioned pharmaceutical compositions are usually formulated in dosage unit form, the unit dose being 100 mg to 1 g. However, if necessary, the daily dose may be increased without danger, due to the low toxicity of compound I and its pharmaceutical suitable salts.

Hereinafter, a few galenic formulations in dosage unit form are given, suitable for systematic administration to human beings in accordance with the present invention. These examples are given as non limiting illustrations of the aforementioned pharmaceutical compositions. In these examples, the active product is designated by "compound A", which is either 2-pentanoylaminoacetic acid either sodium 2-pentanoylaminoacetate.

| Tablets. | |
|---|---|
| Compound A | 500 mg |
| corn starch | 34 mg |
| Silartex$^R$ | 25 mg |
| Aerosil$^R$ | 1 mg |
| Pharmacoat 606$^R$ | 15 mg |

| Tablets. | |
|---|---|
| Compound A | 300 mg |
| starch Sta-RX 1500$^R$ | 180 mg |
| calcium phosphate | 100 mg |
| aerosil$^R$ | 5 mg |
| magnesium stearate | 15 mg |

| Tablets. | |
|---|---|
| Compound A | 100 mg |
| corn starch | 100 mg |

| | |
|---|---|
| -continued | |
| lactose | 188 mg |
| aerosil<sup>R</sup> | 5 mg |
| talc | 5 mg |
| magnesium stearate | 2 mg |
| Capsules. | |
| Compound A | 100 mg |
| lactose | 110 mg |
| corn starch | 20 mg |
| magnesium stearate | 12 mg |
| gelatin | 8 mg |
| Capsules. | |
| Compound A | 200 mg |
| polyvinylpyrrolidone | 10 mg |
| corn starch | 100 mg |
| cutina HR<sup>R</sup> | 10 mg |
| I.M. or I.V. injectables. | |
| Compound A | 100 mg |
| sodium chloride | 20 mg |
| sodium acetate | 6 mg |
| distilled water for ad injectables | 5 ml |
| I.M. injectables. | |
| Compound A | 200 mg |
| benzylbenzoate | 1 mg |
| oil for injection ad | 5 ml |
| Syrup (containing a unit dose of 100 mg per milliliters). | |
| Compound A | 5 g |
| citric acid | 0.5 g |
| nipasept<sup>R</sup> | 0.1 g |
| saccharose | 70 g |
| flavouring agent | 0.1 g |
| water ad | 100 ml |
| Solution (containing a unit dose of 100 mg per milliliters). | |
| Compound A | 2 g |
| sorbitol | 50 g |
| glycerin | 10 g |
| anise essence | 0.1 g |
| propylene glycol | 10 g |
| demineralized water ad | 100 ml |
| Suppositories. | |
| Compound A | 250 mg |
| butylhydroxanisol | 10 mg |
| semi-synthetic glycerids ad | 3 g |

R = registered trademark.

We claim:

1. A method for treating epilepsy, dyskinesiae, Parkinsonism, memory troubles, depression or cerebral anoxia, which comprises administering to a host in need for such a treatment a therapeutically effective amount of 2-pentanoylaminoacetic acid or a pharmaceutically acceptable salt thereof as the therapeutically active substance optionally with a pharmaceutically acceptable carrier or diluent.

2. The method according to claim 1 in which the active substance is administered orally, parenterally or rectally at a daily dose of 100 mg to 5 g.

3. A method for treating epilepsy comprising administering to a person in need of such treatment a therapeutically effective amount of 2-pentanoylaminoacetic acid or a pharmaceutically acceptable salt thereof together with a pharmaceutically acceptable carrier or diluent.

4. The method according to claim 3 in which the pharmaceutically acceptable salt is sodium 2-pentanoylaminoacetate.

5. The method according to claim 3 in which the therapeutically effective amount is from 100 mg to 5 g daily.

6. The method according to claim 5 in which the administration is orally.

7. The method according to claim 5 in which the administration is rectally.

8. The method according to claim 5 in which the administration is parenterally.

* * * * *